Figure 1:
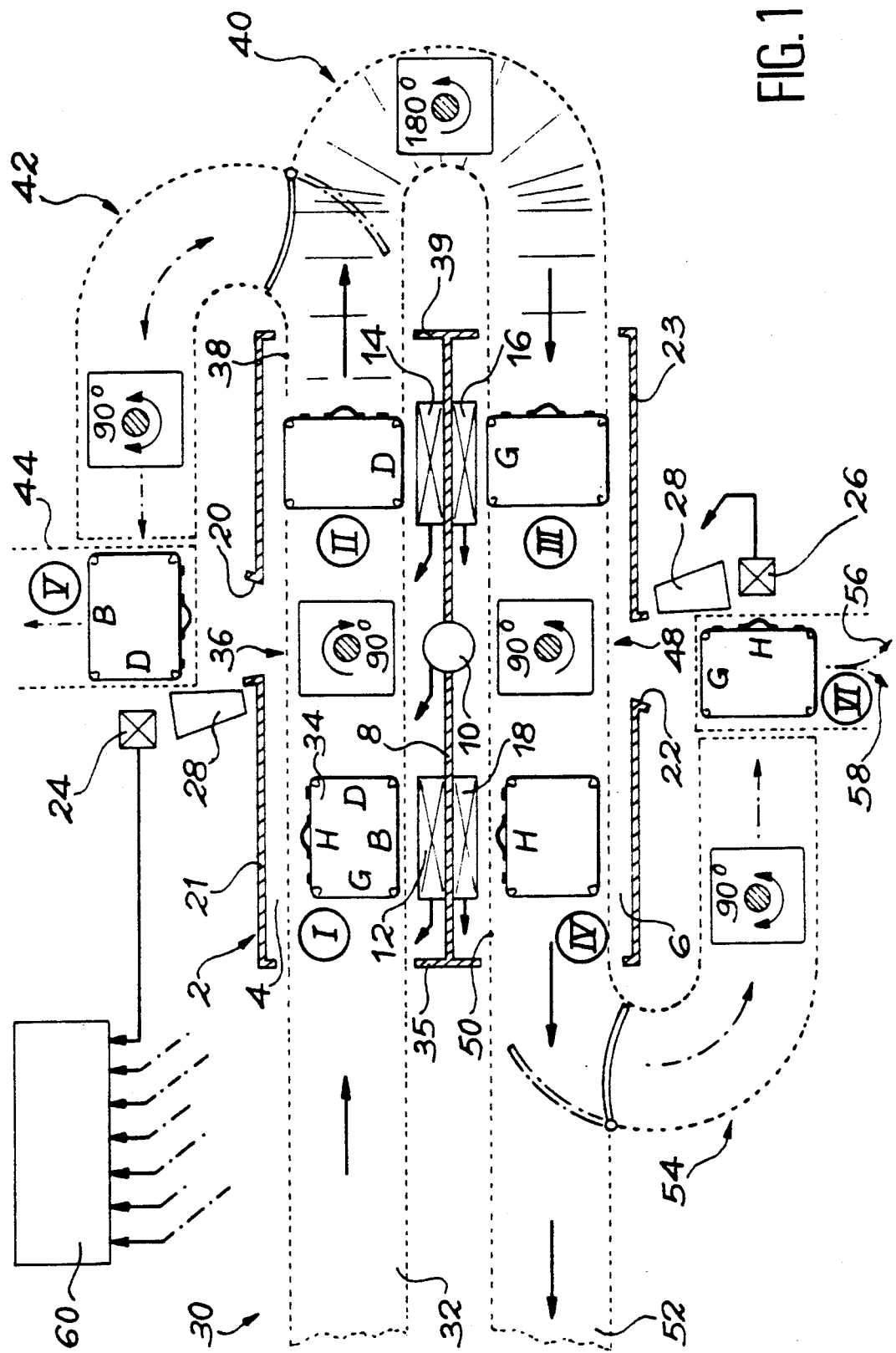

United States Patent [19]

Grenier et al.

[11] Patent Number: 5,080,856
[45] Date of Patent: Jan. 14, 1992

[54] APPARATUS FOR THE DETECTION OF SUBSTANCES AND IN PARTICULAR EXPLOSIVES BY NEUTRON IRRADIATION THEREOF

[75] Inventors: Gérard Grenier, Limeil-Brevannes; Roger H. Coursant, Paris; Michel Rambaut, Bures Sur Yvette, all of France

[73] Assignees: Commissariat A L'Energie Atomique, Paris, France; Sodern Societe D'Etudes et de Realisations Nucleaires, Limeil Brevannes Cedex, both of France

[21] Appl. No.: 688,707

[22] Filed: Apr. 23, 1991

Related U.S. Application Data

[63] Continuation of Ser. No. 374,987, Jul. 3, 1989, abandoned.

[30] Foreign Application Priority Data

Jan. 13, 1989 [FR] France ............... 89 00384

[51] Int. Cl.⁵ ................ G21G 1/06; G01T 3/00
[52] U.S. Cl. ................ 376/159
[58] Field of Search ............ 376/159, 157, 257

[56] References Cited

U.S. PATENT DOCUMENTS

| | | | |
|---|---|---|---|
| 2,938,119 | 5/1960 | McKay | 250/390 C |
| 3,124,679 | 3/1964 | Tittman et al. | 250/390 C |
| 3,146,349 | 8/1964 | Jordan | 250/390 C |
| 3,315,077 | 4/1967 | Jones, Jr. et al. | 250/390 C |
| 3,463,922 | 8/1969 | Senftle et al. | 250/363 |
| 3,781,556 | 12/1973 | Taylor et al. | 376/159 |
| 3,812,364 | 5/1974 | Higatsberger et al. | 250/390 C |
| 3,832,545 | 8/1974 | Bartko | 250/367 |
| 3,942,003 | 3/1976 | Apenberg et al. | 250/390 C |
| 3,997,787 | 12/1976 | Fearon et al. | 250/359.1 |
| 4,024,393 | 5/1977 | Braun et al. | 250/390 C |
| 4,028,267 | 6/1977 | Christell et al. | |
| 4,251,726 | 2/1981 | Alvarez | 376/157 |
| 4,268,754 | 5/1981 | Srapeniants et al. | 250/390 C |
| 4,278,885 | 7/1981 | Alfthan et al. | 376/159 |
| 4,291,227 | 9/1981 | Caldwell et al. | 250/390 C |
| 4,314,155 | 2/1982 | Sowerby | 250/390 C |
| 4,851,687 | 7/1989 | Ettinger et al. | 376/159 |

FOREIGN PATENT DOCUMENTS

295893 1/1972 Austria.

OTHER PUBLICATIONS

Lecture presented to Fifth International Civil Aviation Security Conference, "Equipment for Detection of Explosives by Neutron Activation", J. R. Huriet et al., pp. 1–9, Washington, D.C., Oct. 1988.
Nucleonics, Sep. 1965, pp. 70–78, Tilbury et al.
Pure and Appl. Chem., vol. 49, pp. 1555–1573, (1977), Gijbels et al.
*Modern Methods for Trace Element Analysis*, Ann Arbor Sci. Pub. Inc. 1978, Chap. 9, pp. 370, 371, 390, 391, 398–403, Pinta Radiochem. Radioanal. Letters, vol. 12, No. 4–5, (1972), pp. 283–288, Anisimov et al.

Primary Examiner—Harvey E. Behrend
Attorney, Agent, or Firm—Oblon, Spivak, McClelland, Maier & Neustadt

[57] ABSTRACT

According to the invention, the object (34) is brought to a first inspection station (I to IV) in which the object is irradiated by thermal neutrons, the capture gamma radiation then liable to be emitted by the object and characterizing a chemical element of the substance to be detected is detected, if the intensity of said radiation exceeds a predetermined threshold, the object is brought to a second inspection station (V,VI), in which the object is irradiated by fast neutrons and the prompt gamma radiation then liable to be emitted by the object and characterizing the chemical element is detected, the energy of the fast neutrons being at least equal to that of prompt gamma radiation, in order to confirm or disprove the information obtained in the first station.

11 Claims, 2 Drawing Sheets

APPARATUS FOR THE DETECTION OF SUBSTANCES AND IN PARTICULAR EXPLOSIVES BY NEUTRON IRRADIATION THEREOF

This application is a Continuation of application Ser. No. 07/374,987, filed on Jul. 3, 1989, now abandoned.

DESCRIPTION

The present invention relates to a process and to an apparatus for the detection of substances and in particular explosives by neutron irradiation thereof. It more particularly applies to the inspection of baggage, particularly in airports.

A method for the detection of explosives is already known, which involves the irradiation thereof by thermal neutrons. However, this known method suffers from the disadvantage of giving rise to an excessive percentage of false alarms during high speed inspections and for small explosive quantities.

The object of the present invention is to obviate this disadvantage and therefore reduce the percentage of false alarms by using a double inspection, namely an inspection using thermal neutrons and then an inspection using fast neutrons.

More specifically, the present invention firstly relates to a process for the detection of a substance liable to be contained in an object, characterized in that it comprises the stages of bringing the object to a first inspection station, where the object is irradiated by thermal neutrons, the capture gamma radiation liable to be emitted by the object and characterizing a chemical element of the substance is detected, if the intensity of this capture gamma radiation exceeds a predetermined threshold the object is brought to a second inspection station, where the object is irradiated with fast neutrons and detection takes place of the prompt gamma radiation liable to be emitted by the object and characterizing the chemical element, the energy of the fast neutrons being at least equal to that of the prompt gamma radiation characterizing the chemical element, in order to confirm or disprove the information obtained at the first station.

The present invention also relates to an apparatus for the detection of a substance liable to be contained in an object, characterized in that it comprises means for bringing the object to a first inspection station, first irradiation means for irradiating said object in said first station by thermal neutrons, first detection means for detecting the capture gamma radiation liable to be emitted by the object and characterizing a chemical element in the substance, means for bringing the object to a second inspection station if the intensity of said capture gamma radiation exceeds a predetermined threshold, second irradiation means for irradiating the object in said second station by fast neutrons and second detection means for detecting the prompt gamma radiation liable to be emitted by the object and characterizing the chemical element, the energy of the fast neutrons being at least equal to that of the prompt gamma radiation characterizing the chemical element, in order to confirm or disprove the information obtained at the first station.

In the present invention, there is consequently a first inspection of the object by thermal neutrons and if said inspection is positive (exceeding the threshold), this indicates the possibility of the presence of the substance in the object. A second inspection is then carried out at a different location as compared with the first inspection station using fast neutrons with a view to confirming or disproving the information obtained during the first inspection.

Admittedly document (1) FR-A-2201765 (cf. also U.S. Pat. No. 3,832,545), to which reference should be made, discloses a method for the detection of nitro explosives, using an irradiation by fast neutrons of an object liable to contain the explosive and the detection of the capture gamma radiation which is characteristic of nitrogen and which is emitted by the object if it contains the explosive.

In addition, document (2) EP-A-0227497 published on July 1 1987 and to which reference should be made, discloses another method for the detection of nitro explosive using an irradiation of an object liable to contain the explosive, by fast neutrons and the detection of the prompt gamma radiation which is characteristic of the nitrogen and which is emitted by the object if it contains the explosive.

However, on reading these documents, there is nothing to suggest carrying out two inspections at two separate locations. On the contrary, p. 6, line 35 to p. 7, line 6 of document (2) teaches the possibility of carrying out an inspection of the nitrogen by means of fast neutrons and, at the same location, an inspection of other elements, e.g. chlorine, by means of thermal neutrons resulting from the slowing down of the fast neutrons by the inspected object.

The methods of documents (1) and (2), considered separately, do not make it possible to obtain both a low false alarm level, a high inspection rate and a detection of small quantities of explosive, which is made possible by the present invention.

According to a first embodiment of the apparatus according to the invention, said apparatus comprises an enclosure made from a material able to thermalize the fast neutrons, the first station being located within said enclosure and a fast neutron source, which is located in the enclosure and which is common to the first and second irradiation means and which cooperates with the enclosure to produce the thermal neutrons and in that the enclosure is provided with at least one opening for permitting the passage of part of the fast neutrons emitted by the source, the second station being located outside the enclosure facing the opening.

Preferably, the fast neutron source is a pulsed source for supplying fast neutron bursts, the first detection means serving to detect the capture gamma radiation between the neutron bursts and the second detection means serve to detect the prompt gamma radiation coinciding with said neutron bursts.

The use of a pulsed neutron source, a synchronous detection of the prompt gamma photons and an antisynchronous detection of the capture gamma photons makes it possible to obtain, for each detection type, a signal-to-noise ratio much higher than that obtained with a continuous fast neutron source.

According to a second embodiment of the apparatus according to the invention, said apparatus comprises an enclosure made from a material able to thermalize the fast neutrons, the first station being located within said enclosure and a first fast neutron source placed in the enclosure and which cooperates therewith to produce the thermal neutrons and in that the second irradiation means have at least one fast neutron source, the second station being located outside the enclosure in the vicinity of the second fast neutron source.

Preferably, the first fast neutron source is a pulsed source for supplying fast neutron bursts, the first detection means serving to detect the capture gamma radiation between these neutron bursts and in that the second fast neutron source is also a pulsed source for supplying fast neutron bursts, the second detection means serving to detect the prompt gamma radiation coinciding with the fast neutron bursts supplied by the second source.

The use of a first and a second pulsed sources, which are regulatable independently of one another, makes it possible to optimize the signal-to-noise ratio for each detection type (synchronous and anti-synchronous), which is not made possible through the use of a single pulsed source.

The energy of the fast neutrons is preferably approximately 14 MeV. Thus, a neutron source with such an energy makes it possible to inspect most elements.

In a particular embodiment of the apparatus according to the invention, the first detection means have at least one array of gamma radiation detectors and means for processing the signals supplied by these detectors, said processing means being able to supply a cartography of the object relative to its content of the element.

Said chemical element can be nitrogen, the first detection means then serving to detect gamma radiation at 10.83 MeV of the nitrogen and the second detection means for detecting gamma radiation at 5.106 MeV of the nitrogen. The first detection means can also detect at least one other capture gamma radiation characterizing a material able to stop thermal neutrons. In this case, when the substance is an explosive containing nitrogen, the second detection means can also be provided for detecting at least one other prompt gamma radiation characterizing another element in the substance, e.g. oxygen and/or carbon.

The invention is described in greater detail hereinafter relative to non-limitative embodiments and the attached drawings, wherein show:

FIG. 1 a diagrammatic view of a first embodiment of the apparatus according to the invention, provided with an enclosure shown in plan view and whose upper wall is not shown.

Figure 2:
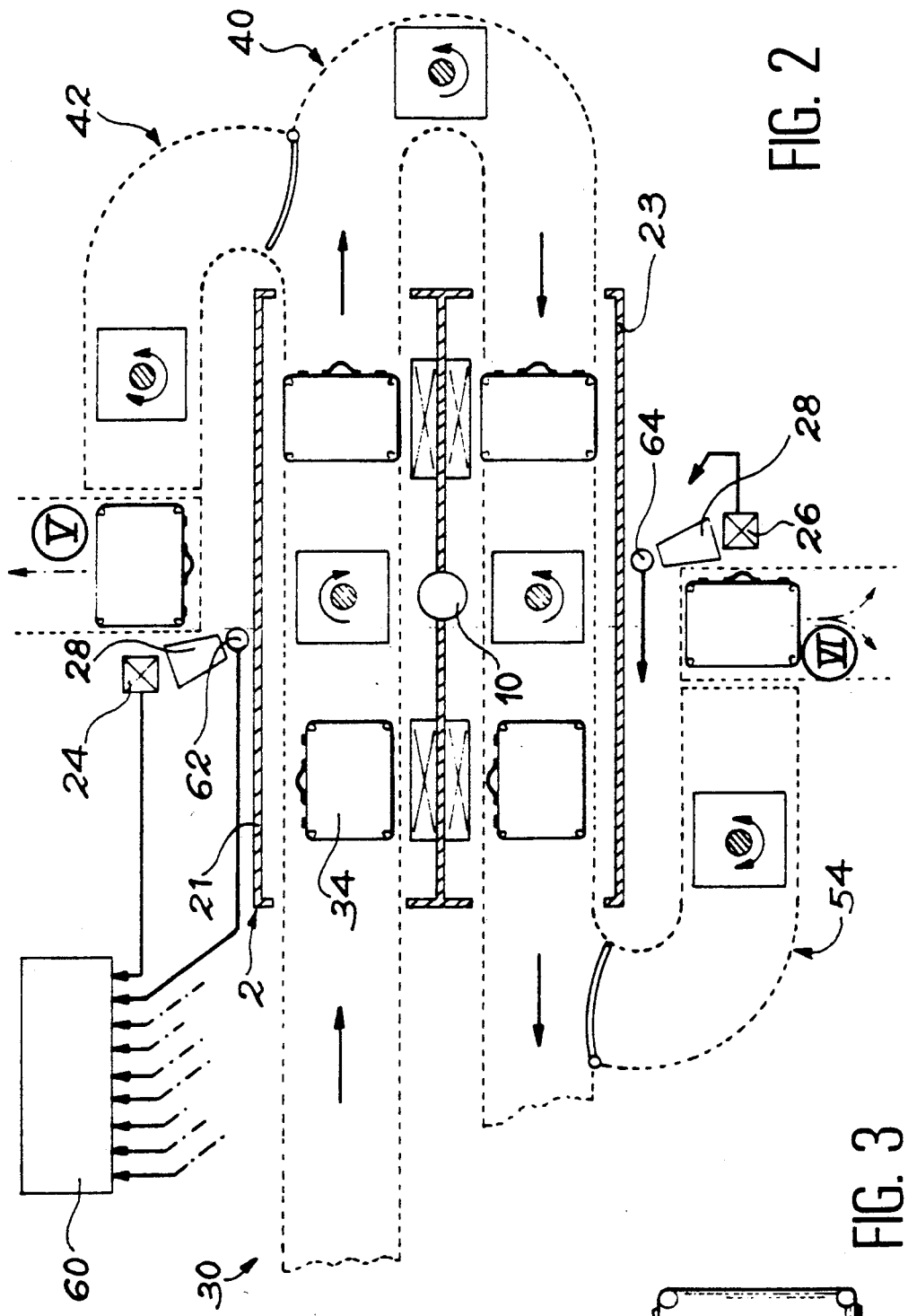

FIG. 2 a diagrammatic view of a second embodiment of the apparatus according to the invention.

Figure 3:
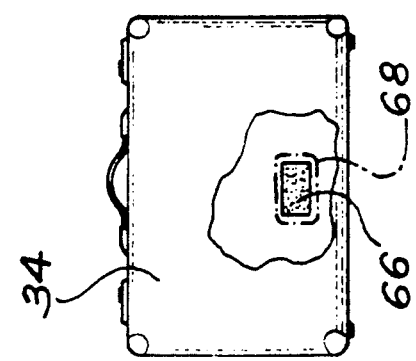

FIG. 3 diagrammatically a constructional variant of the invention.

Hereinafter, it is assumed that it is wished to inspect or check baggage or luggage liable to contain nitro explosives.

The apparatus diagrammatically shown in FIG. 1 comprises a thermalization enclosure 2, which is subdivided into two compartments 4 and 6 by an inner wall 8. The enclosure 2 and its separating wall 8 are made from a material able to thermalize fast neutrons, e.g. a hydrogen-containing material such as polyethylene.

In enclosure 2, the apparatus also comprises a fast neutron source 10, e.g. a tube generating neutrons of 14 MeV by D-T reaction, operating in the pulsed mode and of the type manufactured e.g. by the SODERN company. In its centre, wall 8 has an opening in which is located the source 10, so as to be able to supply fast neutrons into each of the two compartments 4 and 6. These fast neutrons are then thermalized by the walls of the enclosure in such a way that a thermal neutron flux is obtained in each of the two compartments 4 and 6.

The apparatus also comprises four arrays of detectors able to more particularly detect capture gamma photons of 10.83 MeV characteristic of the nitrogen contained in the explosives which it is wished to detect. In a purely indicative and non-limitative manner, each array e.g. comprises 7×5 bismuth germanate (BGO) scintillator detectors and forms a 80×60 cm rectangle, which makes it possible to inspect luggage on four sides opposing one another in pairs, each side having as its maximum dimensions 80×60 cm. These arrays carry the respective references 12, 14,16 and 18 in FIG. 1. The arrays 12 and 14 are placed in compartment 4, against wall 8 and equidistant with respect to source 10. Arrays 16 and 18 are placed in compartment 6, against wall 8 and equidistant with respect to source 10 and respectively level with arrays 14 and 12. Thus, in enclosure 2 are defined first, second, third and fourth inspection stations respectively located facing the four arrays 12,14,16 and 18.

Compartments 4 and 6 communicate with the outside of enclosure 2 respectively by the openings 20 and 22. Openings 20 and 22 are respectively located on enclosure walls 21,23 facing the inner wall 8. Openings 20 and 22 are aligned with source 10, so that on one side of their alignment line is located the first station I and the fourth station IV and on the other side the second station II and the third station III. Each of these two openings 20,22 permits part of the fast neutrons produced by the source 10 to pass outside enclosure 2.

A fifth inspection station V and a sixth inspection station VI are positioned outside enclosure 2, respectively facing and in the vicinity of openings 20 and 22. A detector 24 or respectively 26 able to detect prompt gamma photons of 5.106 MeV characteristic of nitrogen is placed in the vicinity of station V or VI. It is a high resolution detector, e.g. a high purity germanium detector. Each of the detectors 24 and 26 is protected against the neutron radiation from enclosure 2 (and essentially source 10) by an appropriate protection element 28, which separates the said detector from the wall of the enclosure which it faces and which widens in the direction of the detector.

The apparatus shown in FIG. 1 also comprises means 30 for moving the luggage to be inspected, said luggage items arriving individually at the apparatus for individual inspection by the same.

The means 30 comprise:
  means 32 for bringing a luggage item 34 into compartment 4 at station I through an opening provided on wall 35 linking walls 21 and 23 and located on the side of stations I and IV, in such a way that the baggage item 34 presents a side carrying reference B to array 12,
  means 36 for bringing the luggage to station II with a 90° pivoting between stations I and II, in such a way that the baggage presents to array 14 a side D adjacent to side B,
  means 38 for removing the baggage from compartment 4 by an opening provided on wall 39 linking walls 21 and 23 and located on the side of stations II and III,
  means 40 for bringing the baggage which has left station III through another opening provided on wall 39, whilst making the baggage describe a 180° turn, with also a 180° pivoting movement in the direction opposite to that of the turn, so that the baggage presents to array 16 side G opposite to side D, means 42 for bringing to the station V the baggage which has left compartment 4, in such a way that its side B or its side D, as a function of the particular case, is turned towards the detector 24 and for bringing it on leaving compartment 4 into the position which it occupied in station II, means 44 for bringing the baggage to a "suspect baggage" area from station V, means 48 for bringing the baggage from station III to station IV with a 90° pivoting movement between the stations, in such a way that the baggage presents to array 18 side H opposite to side B, means 50 for removing the baggage from compartment 6 through another opening in wall 35, means 52 for bringing the baggage which has left the "inspected baggage" zone, means 54 for bringing the thus removed baggage to station VI, in such a way that the baggage presents its side G or its side H, as a function of the particular case, to detector 26, means 56 for bringing the baggage to the "suspect baggage" area from station VI, means 58 for bringing the baggage from station VI to the "inspected baggage" area.

The apparatus also comprises means 60 for the processing of signals supplied by the various detectors and for controlling the displacement means 30 of the baggage 34 to be inspected.

It should be noted that means 60 are connected to arrays 12, 14, 16, 18, to detectors 24 and 26 and, by a synchronization line, to the pulsed source 10, with a view to carrying out the detection of prompt gamma photons coinciding with the fast neutron bursts and the detection of the capture gamma photons between said neutron bursts.

The apparatus shown in FIG. 1 operates as follows. Baggage 34 is brought from a baggage storage area to station I, where it is irradiated with thermal neutrons resulting from the thermalization, by the walls of enclosure 2, of the 14 MeV neutrons emitted by source 10, then brought to station II, where the baggage undergoes the same irradiation. The information supplied by each of the arrays 12 and 14 to means 60, during the examination in the corresponding station, are processed there in order to obtain a partial cartography in numerical or digital form of the particular baggage item, said partial cartography being quantified by its nitrogen content relative to a first detection threshold taking account, in its definition, of the sensitivity of the equipment in the detection mode used, the probability of a false alarm and the probability of non-detection in a desired form.

If the threshold is not reached in either of the two inspections the baggage item is supplied to station III and then to station IV, where it undergoes the same examination as in stations I and II, which makes it possible to obtain the complete cartography thereof. If once again the threshold is not reached in any of the examinations performed in stations III and IV, the baggage is considered none-suspect and is dispatched to the inspected baggage area.

If the threshold is reached or exceeded during one of the inspections in stations I and II, the baggage item is passed to station V. If it is a case of the examination in station I or II, the baggage is brought to station V with an orientation such that side B or side D thereof faces detector 24. The baggage then undergoes irradiation by fast neutrons. The information then supplied by detector 24 to means 60 is processed therein and compared with a second detection threshold. If the latter is not reached, the baggage is supplied on leaving compartment 4 the position which it occupied in station II and from there to station III for continuing the inspection. However, if the second threshold is exceeded or reached, the baggage is considered suspect and is passed to the suspect baggage storage area.

If the threshold is reached during one of the examinations in stations III and IV, the baggage is supplied to station VI. In the case of the examination in station III or IV, the baggage is supplied to station VI with an orientation such that side G or H of the baggage faces detector 26. The baggage then undergoes the same inspection as that carried out in station V. If the second threshold is not reached, it is considered that the baggage is not suspect. However, if the second threshold is reached or exceeded, the baggage is considered suspect and is passed to the suspect baggage storage area.

The apparatus diagrammatically shown in FIG. 2 differs from that shown in FIG. 1 by the fact that the openings 20 and 22 are eliminated and it has, apart from source 10, two other pulsed fast neutron sources 62 and 64, whose neutron fluxes can advantageously be lower (approximately 10 to 100 times) than the flux supplied by source 10, sources 62 and 64 being less expensive than source 10.

The means 60 are in this case provided for carrying out the detection of prompt gamma photons produced by station V coinciding with the fast neutron bursts emitted by source 62 and for carrying out the detection of the prompt gamma photons produced by station VI coinciding with the fast neutron bursts emitted by source 64, as well as for carrying out the detection of the capture gamma photons produced in any one of the stations I to IV between the fast neutron bursts emitted by source 10 and for this purpose are connected by a synchronization line to each of the sources 10, 62 and 64.

Source 62 or 64 is placed close to the protecting element corresponding to detector 24 or 26 opposite thereto with respect to the element provided in the case of FIG. 2 for protecting the corresponding detector not only from the neutron radiation of source 10, but also the neutron radiation of the corresponding source 62 or 64.

As can be seen in FIG. 3, the explosive 66 which may be contained in the baggage to be inspected 34 may have been placed in an envelope 68 made from a material able to stop thermal neutrons. In order to get round this possibility, in each of the stations I to IV, there can not only be an acquisition of the radiation at 10.83 MeV of nitrogen, but also at least one other capture gamma radiation, each other capture gamma radiation characterizing a material able to stop thermal neutrons. Then, if the first threshold relative to nitrogen is reached or exceeded or if the intensity of one of the other capture gamma radiation exceeds a certain level fixed by the users, the baggage is passed to station V or VI for a complimentary examination by fast neutrons in the manner explained hereinbefore.

In stations V and VI, apart from the nitrogen inspection, it is also possible to carry out a detection of prompt gamma radiations characterizing oxygen and carbon and to determine the relative atomic percentages of oxygen and nitrogen, as well as carbon and nitrogen in the baggage, in order to compare these percentages respectively with the N/O and C/O ratios of known explosives.

The present invention is not limited to the detection of nitro explosives. It is also applicable to the detection of non-nitro explosives, such as e.g. ($KClO_3$+reducing agent) or ($KMnO_4$+reducing agent) complexes. In this case other elements are detected, whilst exploiting with the aid of the capture reactions, the followin gamma signatures.

| Elements | Effective Section (barns) | Energy of the gammas emitted (MeV) | Relative Intensity |
|---|---|---|---|
| Cl | 33 | 6.1 | 20% |
|  |  | 1.95 | 22% |
| Mn | 13 | 7.2 | 12% |
|  |  | 7.06 | 11% |
| K | 2.1 | 0.77 | 51% |
|  |  | 2 | 11% |
| S | 0.52 | 5.4 | 59% |
| Na | 0.4 | 6.4 | 22% |
|  |  | 3.28 | 19% |
| P | 0.18 | 3.9 | 16% |
|  |  | 2.15 | 15% | and with the aid of inelastic interactions, the following gamma signatures, whose energies are given in MeV:

| | |
|---|---|
| Cl: | 1.22–1.73–1.76–2.64–2.69 |
| Mn: | 0.86–1.17–1.53–1.88 |
| K: | 0.28–1.27–1.29–2.81–3.02 |
| S: | 1.27–1.68–2.03–2.13–2.23 |
| Na: | 1.64–2.39–2.64–2.98 |
| P: | 1.27–2.03–2.15–2.23–3.13 |

The present invention also applies to the detection of narcotics utilizing inter alia carbon and nitrogen signatures.

The present invention is also applicable to the field of real time non-destructive testing on an operational site and also to the field of the optimized control of industrial processes. It should be noted that the apparatus according to the invention can be entirely automated.

We claim:

1. Apparatus for the detection of a substance liable to be contained in an object (34) comprising:
   a first inspection station (I to IV),
   first irradiation means (2, 10) for irradiating said object at said first station by thermal neutrons,
   first detection means (12, 14, 16, 18) for detecting at least one capture gamma radiation liable to be emitted by the object due to thermal neutron irradiation thereof, said capture gamma radiation characterizing a chemical element in the substance,
   a second inspection station (V, VI),
   second irradiation means (10 or 62, 64) for irradiating the object at said second station by fast neutrons,
   second detection means (24, 26) for detecting at least one prompt gamma radiation liable to be emitted by the object due to fast neutron irradiation thereof, said prompt gamma radiation characterizing the chemical element, and the energy of the fast neutrons being at least equal to that of the prompt gamma radiation characterizing the chemical element,
   displacement means (30), said displacement means having
      means for bringing the object to the first inspection station (I to IV),
      means for bringing the object from the first inspection station to the second inspection station (V, VI),
      means for bringing the object from the first inspection station to a first area,
      means for bringing the object from the second inspection station to a second area, and
   processing and control means (60) for comparing the intensity of said capture gamma radiation and the intensity of said prompt gamma radiation to a predetermined threshold and to another predetermined threshold respectively, and for controlling the displacement means, so as to displace the object from the first inspection station to one of the first area, if the intensity of said capture gamma radiation is lower than said predetermined threshold, and the second inspection station, if the intensity of said capture gamma radiation is equal to or greater than said predetermined threshold, and from the second inspection station to one of the first area, if the intensity of said prompt gamma radiation is lower than said other predetermined threshold, and the second area, if the intensity of said prompt gamma radiation is equal to or greater than said other predetermined threshold.

2. Apparatus according to claim 1, further comprising:
   an enclosure (2) made from a material for thermalizing the fast neutrons, the first station being located within said enclosure; and
   a fast neutron source (10), which is located in the enclosure and which is common to the first and second irradiation means and which cooperates with the enclosure to produce the thermal neutrons;
   wherein the enclosure is provided with at least one opening (20, 22) for permitting passage of part of the fast neutrons emitted by the fast neutron source, the second station being located outside the enclosure and facing the opening.

3. Apparatus according to claim 2, wherein the fast neutron source (10) is a pulsed source for supplying fast neutron bursts, the first detection means including means for detecting capture gamma radiation between the neutron bursts and the second detection means includes means for detecting prompt gamma radiation coinciding with the neutron bursts.

4. Apparatus according to claim 1, further comprising:
   an enclosure (2) made from a material for thermalizing the fast neutrons, the first station being located within said enclosure, and
   a first fast neutron source (10) which is placed in the enclosure and which cooperates therewith to produce the thermal neutrons;
   wherein the second irradiation means includes at least one second fast neutron source, the second station being located outside the enclosure in the vicinity of the second fast neutron source (62, 64).

5. Apparatus according to claim 4, wherein the first fast neutron source is a pulsed source (10) for supplying fast neutron bursts, the first detection means including means for detecting the capture gamma radiation between the fast neutron bursts and wherein the second fast neutron source (62, 64) is a pulsed source for supplying fast neutron bursts, the second detection means including means for detecting the prompt gamma radiation coinciding with the fast neutron bursts supplied by the second source.

6. Apparatus according to claim 1, wherein energy of the fast neutrons is approximately 14 MeV.

7. Apparatus according to claim 1, wherein the first detection means incorporates at least one array of gamma radiation detectors (12, 14, 16, 18) and signal processing means (60) for processing the signals supplied by the at least one array of gamma radiation detectors, said signal processing means including means for supplying a cartography of the object relative to an element content of said chemical element thereof.

8. Apparatus according to claim 1, wherein said chemical element is nitrogen, wherein the first detection means includes means for detecting gamma radiation, at 10.83 MeV, of nitrogen and wherein the second detection means includes means for detecting gamma radiation, at 5.106 MeV, of nitrogen.

9. Apparatus according to claim 1, wherein said chemical element is nitrogen, wherein the first detection means includes means for detecting gamma radiation at 10.83 MeV of nitrogen and for detecting at least one other capture gamma radiation characterizing a material able to stop thermal neutrons and wherein the second detection means includes means for detecting gamma radiation at 5.106 MeV of nitrogen.

10. Apparatus according to claim 8, wherein the substance is an explosive containing nitrogen, the second detection means including means for detecting at least one other prompt gamma radiation characterizing another element of the substance.

11. Apparatus according to claim 9, wherein the substance is an explosive containing nitrogen, the second detection means includes means for detecting at least one other prompt gamma radiation characterizing another element of the substance.

* * * * *